US011492386B2

(12) United States Patent
Korytko et al.

(10) Patent No.: US 11,492,386 B2
(45) Date of Patent: Nov. 8, 2022

(54) PARATHYROID HORMONE-ANTI-RANKL ANTIBODY FUSION COMPOUNDS

(71) Applicant: Eli Lilly and Company, Indianapolis, IN (US)

(72) Inventors: Andrew H Korytko, Oceanside, CA (US); Yanfei L Ma, Carmel, IN (US); Amita Datta-Mannan, Indianapolis, IN (US); Victor H Obungu, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 850 days.

(21) Appl. No.: 16/071,326

(22) PCT Filed: Jan. 25, 2017

(86) PCT No.: PCT/US2017/014836
§ 371 (c)(1),
(2) Date: Jul. 19, 2018

(87) PCT Pub. No.: WO2017/136195
PCT Pub. Date: Aug. 10, 2017

(65) Prior Publication Data
US 2020/0354427 A1 Nov. 12, 2020

Related U.S. Application Data

(60) Provisional application No. 62/289,572, filed on Feb. 1, 2016.

(51) Int. Cl.
*C07K 14/635* (2006.01)
*A61P 19/08* (2006.01)
*C07K 16/46* (2006.01)

(52) U.S. Cl.
CPC ............ *C07K 14/635* (2013.01); *A61P 19/08* (2018.01); *C07K 16/461* (2013.01)

(58) Field of Classification Search
None
See application file for complete search history.

(56) References Cited

U.S. PATENT DOCUMENTS

| 6,740,522 | B2 | 5/2004 | Anderson |
| 8,992,925 | B2 * | 3/2015 | Kostenuik ............... A61P 19/08 424/145.1 |
| 2011/0305711 | A1 | 12/2011 | Allan et al. |
| 2012/0294797 | A1 | 11/2012 | Kovacevich et al. |

FOREIGN PATENT DOCUMENTS

| WO | 2000/010596 A1 | 3/2000 |
| WO | 2007/059136 A2 | 5/2007 |
| WO | 2007054809 A2 | 5/2007 |
| WO | 2009109911 A1 | 9/2009 |
| WO | 2015125922 | 8/2015 |
| WO | WO-2016186957 A1 * | 11/2016 ............ C07K 16/18 |

OTHER PUBLICATIONS

Vajdos et al. (J Mol Biol. Jul. 5, 2002;320(2):415-28) (Year: 2002).*
Brown et al. (J Immunol. May 1996;156(9):3285-91) (Year: 1996).*
Kabat, et al., Ann. NY Acad. Sci. 190:382-93 (1971).
North et al., A New Clustering of Antibody CDR Loop Conformations, Journal of Molecular Biology, 406:228-256 (2011).
Furuya, et al. "Increased Bone Mass in Mice after single injection of Anti-receptor Activator of Nuclear Factor-B Ligand-neutralizing Antibody: Evidence for bone anabolic effect of parathyroid hormone in mice with few osteoclasts", Journal of Biological Chemistry, vol. 286, No. 42, Oct. 21, 2011.
Tokuyama, N., et al. "Individual and combining effects of anti-RANKL monoclonal antibody and teriparatide in ovariectomized mice." Bone reports 2 (2015): 1-7.
European Patent Office. Examination report for application 17704359. 3, dated Feb. 11, 2020.
International Searching Authority, International Preliminary Report on Patentability for application PCT/US2017/014836, dated Aug. 7, 2018.
Japan Patent Office. Official Action for application 2018-539096. dated Mar. 3, 2020. With translation.
Canadian Intellectual Property Office. Office Action for application 3,013,443, dated May 11, 2020.
Hu, F. et al., "Fasting serum CGRP levels are related to calcium concentrations, but cannot be elevated by short-term calcium/vitamin D supplementation," Neuropeptides, 2015, vol. 49, pp. 37-45.
Frobert, Y. et al., "A sensitive sandwich enzyme immunoassay for calcitonin gene-related peptide (CGRP): characterization and application," Peptides, 1999, 20(2), pp. 275-284.
Patent Cooperation Treaty International Search Report and Written Opinion of the International Searching Authority pertaining to International Application No. PCT/US2017/014325 (filed Jan. 20, 2017); Date of the actual completion of the International Search Apr. 12, 2017, Date of mailing of the International search report: May 2, 2017.
Zhang, Z. et al., "Plasma level of calcitonin gene-related peptide in patients with polycystic ovary syndrome and its relationship to hormonal and metabolic parameters," Peptides 2012, 34(2), pp. 343-348.

* cited by examiner

*Primary Examiner* — Brian Gangle
*Assistant Examiner* — Andrea K McCollum
(74) *Attorney, Agent, or Firm* — Quarles & Brady LLP

(57) ABSTRACT

Fusion compounds and methods of using same are provided which bind and neutralize human receptor activator of nuclear factor kappa-B ligand and are agonistic to parathyroid hormone receptor 1 signaling, said compounds are useful as agents for bone healing or treating conditions associated with bone mass loss or degeneration including treating osteoporosis.

19 Claims, No Drawings
Specification includes a Sequence Listing.

SEQUENCE LISTING

<160> NUMBER OF SEQ ID NOS: 15

<210> SEQ ID NO 1
<211> LENGTH: 496
<212> TYPE: PRT
<213> ORGANISM: Artificial Sequence
<220> FEATURE:
<223> OTHER INFORMATION: Exemplified First Polypeptide (of exemplified
      fusion compound of Table 1)

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

```
Asn Phe Gly Gly Gly Ser Gly Gly Gly Ser Gly Gly Gly
        35                  40                  45

Ser Gln Val Gln Leu Val Gln Ser Gly Ala Glu Val Lys Lys Pro Gly
50                  55                  60

Ser Ser Val Lys Val Ser Cys Lys Ala Ser Gly Tyr Ala Phe Thr Asn
65                  70                  75                  80

Tyr Tyr Ile Glu Trp Val Arg Gln Ala Pro Gly Gln Gly Leu Glu Trp
                85                  90                  95

Met Gly Val Ile Asn Pro Gly Trp Gly Asp Thr Asn Tyr Asn Glu Lys
                100                 105                 110

Phe Lys Gly Arg Val Thr Ile Thr Ala Asp Lys Ser Thr Ser Thr Ala
                115                 120                 125

Tyr Met Glu Leu Ser Ser Leu Arg Ser Glu Asp Thr Ala Val Tyr Tyr
        130                 135                 140

Cys Ala Arg Arg Asp Thr Ala His Gly Tyr Tyr Ala Leu Asp Pro Trp
145                 150                 155                 160

Gly Gln Gly Thr Thr Val Thr Val Ser Ser Ala Ser Thr Lys Gly Pro
                165                 170                 175

Ser Val Phe Pro Leu Ala Pro Cys Ser Arg Ser Thr Ser Glu Ser Thr
                180                 185                 190

Ala Ala Leu Gly Cys Leu Val Lys Asp Tyr Phe Pro Glu Pro Val Thr
        195                 200                 205

Val Ser Trp Asn Ser Gly Ala Leu Thr Ser Gly Val His Thr Phe Pro
        210                 215                 220

Ala Val Leu Gln Ser Ser Gly Leu Tyr Ser Leu Ser Ser Val Val Thr
225                 230                 235                 240

Val Pro Ser Ser Ser Leu Gly Thr Lys Thr Tyr Thr Cys Asn Val Asp
                245                 250                 255

His Lys Pro Ser Asn Thr Lys Val Asp Lys Arg Val Glu Ser Lys Tyr
                260                 265                 270

Gly Pro Pro Cys Pro Pro Cys Pro Ala Pro Glu Ala Ala Gly Gly Pro
                275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Asn Ser Thr Tyr Arg Val
                340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
        370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
                420                 425                 430

Ser Asn Gly Gln Pro Glu Asn Asn Tyr Lys Thr Thr Pro Pro Val Leu
        435                 440                 445
```

```
Asp Ser Asp Gly Ser Phe Phe Leu Tyr Ser Arg Leu Thr Val Asp Lys
    450                 455                 460
Ser Arg Trp Gln Glu Gly Asn Val Phe Ser Cys Ser Val Met His Glu
465                 470                 475                 480
Ala Leu His Asn His Tyr Thr Gln Lys Ser Leu Ser Leu Ser Leu Gly
                485                 490                 495

<210> SEQ ID NO 2
<211> LENGTH: 214
<212> TYPE: PRT
<213> ORGANISM: Artificial Sequence
<220> FEATURE:
<223> OTHER INFORMATION: Exemplified Second Polypeptide (of the
      exemplified fusion compound of Table 1)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 1491
<212> TYPE: DNA
<213> ORGANISM: Artificial Sequence
<220> FEATURE:
<223> OTHER INFORMATION: DNA Seq. Encoding the Exemplified First
      Polypeptide (SEQ ID NO. 1) and a Signal Peptide

<400> SEQUENCE: 3
agcgtgtccg agatccagct gatgcacaac ctcggcaagc acctgaatag catggagcgc      60
gtcgagtggc tgcggaagaa actgcaggac gtgcacaact cggcggcgg cggcagcggc      120 ggtggcggct ccggtggcgg cggaagccag gtgcagctgg tgcagtctgg ggctgaggtg     180
```

```
aagaagcctg ggtcctcagt gaaggtttcc tgcaaggcat ctggctacgc cttcaccaac      240
tactatatcg agtgggtgcg acaggcccct ggacaagggc ttgagtggat gggagtgatc      300
aaccccggct ggggcgacac gaactacaac gagaagttca agggcagagt caccattacc      360
gcggacaaat ccacgagcac agcctacatg gagctgagca gcctgagatc tgaggacacg      420
gccgtgtatt actgtgcgag acgcgatacg gctcacggct actacgccct tgatccgtgg      480
ggccaaggaa ccacggtcac cgtctcctca gcctccacca agggcccatc ggtcttcccg      540
ctagcgccct gctccaggag cacctccgag agcacagccg ccctgggctg cctggtcaag      600
gactacttcc ccgaaccggt gacggtgtcg tggaactcag gcgccctgac cagcggcgtg      660
cacaccttcc cggctgtcct acagtcctca ggactctact ccctcagcag cgtggtgacc      720
gtgccctcca gcagcttggg cacgaagacc tacacctgca acgtagatca caagcccagc      780
aacaccaagg tggacaagag agttgagtcc aaatatggtc cccatgccc accctgccca      840 gcacctgagg ccgccggggg accatcagtc ttcctgttcc ccccaaaacc caaggacact      900
ctcatgatct cccggacccc tgaggtcacg tgcgtggtgg tggacgtgag ccaggaagac      960
cccgaggtcc agttcaactg gtacgtggat ggcgtggagg tgcataatgc caagacaaag     1020
ccgcgggagg agcagttcaa cagcacgtac cgtgtggtca gcgtcctcac cgtcctgcac     1080
caggactggc tgaacggcaa ggagtacaag tgcaaggtct ccaacaaagg cctcccgtcc     1140
tccatcgaga aaaccatctc caaagccaaa gggcagcccc gagagccaca ggtgtacacc     1200
ctgcccccat cccaggagga tgaccaagaa ccaggtca gcctgacctg cctggtcaaa       1260
ggcttctacc ccagcgacat cgccgtggag tgggaaagca atgggcagcc ggagaacaac     1320
tacaagacca cgcctcccgt gctggactcc gacggctcct tcttcctcta cagcaggcta     1380
accgtggaca gagcaggtg gcaggaggg aatgtcttct catgctccgt gatgcatgag       1440
gctctgcaca accactacac acagaagagc ctctcc ctgt ctctgggttg a             1491

<210> SEQ ID NO 4
<211> LENGTH: 690
<212> TYPE: DNA
<213> ORGANISM: Artificial Sequence
<220> FEATURE:
<223> OTHER INFORMATION: DNA Seq. Encoding the Exemplified Second
      Polypeptide (SEQ ID NO. 2) and a Signal Peptide

<400> SEQUENCE: 4
ggcggcggcg gcagcggcgg tggcggctcc ggtggcggcg gaagcgacat ccagatgacc       60
cagtctccat cctctctgtc tgcatctgta ggagacagag tcaccatcac ttgcaaggcc      120
agccagaatg tgggcaccaa cgtggcctgg tatcagcaga aaccagggaa agcccctaag      180
ctcctgatct atagccag ctacagatac agcggggtcc catcaaggtt cagtggcagt        240
ggatctggga cagatttcac tctcaccatc agcagtctgc aacctgaaga ttttgcaact      300
tactactgtc agcagtactg gactacccc tgaccttcg gcgagggac caaggtggag         360 atcaaacgga ctgtggctgc accatctgtc ttcatcttcc cgccatctga tgagcagttg      420
aaatctggaa ctgcctctgt tgtgtgcctg ctgaataact tctatcccag agaggccaaa      480
gtacagtgga aggtggataa cgccctccaa tcgggtaact cccaggagag tgtcacagag      540
caggacagca aggacagcac ctacagcctc agcagcaccc tgacgctgag caaagcagac      600
tacgagaaac acaaagtcta cgcctgcgaa gtcacccatc agggcctgag ctcgcccgtc      660
acaaagagct tcaacagggg agagtgctaa                                      690
```

```
<210> SEQ ID NO 5
<211> LENGTH: 121
<212> TYPE: PRT
<213> ORGANISM: Artificial Sequence
<220> FEATURE:
<223> OTHER INFORMATION: Exemplified HCVR (of exemplified fusion
      compound of Table 1)

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Tyr Ile Glu Trp Val Arg Gln Ala Pro Gly Gln Gly Leu Glu Trp Met
        35                  40                  45

Gly Val Ile Asn Pro Gly Trp Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Thr Ala His Gly Tyr Tyr Ala Leu Asp Pro Trp Gly
            100                 105                 110

Gln Gly Thr Thr Val Thr Val Ser Ser
        115                 120

<210> SEQ ID NO 6
<211> LENGTH: 107
<212> TYPE: PRT
<213> ORGANISM: Artificial Sequence
<220> FEATURE:
<223> OTHER INFORMATION: Exemplified LCVR (of exemplified fusion
      compound of Table 1)

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Asp Tyr Pro Leu
                85                  90                  95

Thr Phe Gly Gly Gly Thr Lys Val Glu Ile Lys
            100                 105

<210> SEQ ID NO 7
<211> LENGTH: 10
<212> TYPE: PRT
<213> ORGANISM: Artificial Sequence
<220> FEATURE:
<223> OTHER INFORMATION: Exemplified HCDR1 (of exemplified fusion
      compound of Table 1)

<400> SEQUENCE: 7

Gly Tyr Ala Phe Thr Asn Tyr Tyr Ile Glu
```

-continued

```
<210> SEQ ID NO 8
<211> LENGTH: 17
<212> TYPE: PRT
<213> ORGANISM: Artificial Sequence
<220> FEATURE:
<223> OTHER INFORMATION: Exemplified HCDR2 (of exemplified fusion
      compound of Table 1)

<400> SEQUENCE: 8

Val Ile Asn Pro Gly Trp Gly Asp Thr Asn Tyr Asn Glu Lys Phe Lys
1               5                   10                  15
Gly

<210> SEQ ID NO 9
<211> LENGTH: 12
<212> TYPE: PRT
<213> ORGANISM: Artificial Sequence
<220> FEATURE:
<223> OTHER INFORMATION: Exemplified HCDR3 (of exemplified fusion
      compound of Table 1)

<400> SEQUENCE: 9

Arg Asp Thr Ala His Gly Tyr Tyr Ala Leu Asp Pro
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Exemplified LCDR1 (of exemplified fusion
      compound of Table 1)

<400> SEQUENCE: 10

Lys Ala Ser Gln Asn Val Gly Thr Asn Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Exemplified LCDR2 (of exemplified fusion
      compound of Table 1)

<400> SEQUENCE: 11

Ser Ala Ser Tyr Arg Tyr Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Exemplified LCDR3 (of exemplified fusion
      compound of Table 1)

<400> SEQUENCE: 12

Gln Gln Tyr Trp Asp Tyr Pro Leu Thr
1               5

<210> SEQ ID NO 13
<211> LENGTH: 34
<212> TYPE: PRT
<213> ORGANISM: Artificial Sequence
```

```
<220> FEATURE:
<223> OTHER INFORMATION: Exemplified PTH Peptide of exemplified fusion
      compound of Table 1

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 14
<211> LENGTH: 15
<212> TYPE: PRT
<213> ORGANISM: Artificial Sequence
<220> FEATURE:
<223> OTHER INFORMATION: Exemplified Linker of exemplified fusion
      compound of Table 1

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 84
<212> TYPE: PRT
<213> ORGANISM: Artificial Sequence
<220> FEATURE:
<223> OTHER INFORMATION: Full length Human Parathyroid Hormone

<400> SEQUENCE: 15

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln
```

PARATHYROID HORMONE-ANTI-RANKL ANTIBODY FUSION COMPOUNDS

The present invention is in the field of medicine. More particularly, the present invention relates to fusion compounds, and pharmaceutical compositions thereof, which include an agonist of human parathyroid hormone receptors and an antibody directed against human receptor activator of nuclear factor kappa-B ligand (RANKL). The fusion compounds of the present invention are expected to be useful in the treatment of bone disorders, and more particularly in the treatment of low bone mass disorders, including osteopenia, osteogenesis imperfecta, transplant-associated bone loss, autoimmune-induced bone loss, and/or disuse-induced bone loss, and/or in bone healing of disorders such as degenerative lumbar spondylolisthesis or degenerative disk disease as well as bone healing in spinal fusion and fracture patients.

Bone disorders affect millions of individuals, often causing painful and debilitating symptoms. Osteoporosis, a common metabolic bone disorder, is characterized by progressive loss of bone mass resulting, at least in part, from excessive osteoclastic bone resorption relative to osteoblastic bone formation. The loss of bone mass associated with osteoporosis puts bones at a greater risk of fracture Long-term consequences of osteoporosis-associated loss of bone mass can result in severe physical consequences including bone fractures, chronic pain, disability, and/or immobility, as well as rendering the skeleton unable to provide adequate structural support for the body.

Osteoporosis-related fractures constitute a major health concern and economic burden for health care systems According to the National Osteoporosis Foundation, 9.9 million Americans have osteoporosis and an additional 43.1 million suffer from low bone density. Annually, over two million bone fractures and more than four-hundred thousand hospital admissions are attributed to osteoporosis. The U.S. Surgeon General estimates osteoporosis-related bone fractures result in direct care expenditure of between twelve and eighteen billion dollars annually. Thus, there remains a need for alternative therapies which could lead to better outcomes for patients. Preferably such alternative therapy will comprise an agent which both increases bone formation and reduces bone resorption. Additionally, such alternative therapy will preferably be capable of demonstrating efficacy in treatment of low bone mass disorders such as osteopenia, osteogenesis imperfecta, transplant-associated bone loss, autoimmune-induced bone loss, and/or disuse-induced bone loss and/or in bone healing of disorders such as degenerative lumbar spondylolisthesis or degenerative disk disease. The fusion compounds of the present invention provide an alternative therapy which is expected to meet at least one of the above needs.

RANKL is a member of the TNF-superfamily of proteins and plays an important role in bone remodeling. RANKL is expressed by osteoblasts and binds its cognate receptor RANK on the surface of osteoclasts and osteoclast precursor cells. Binding of RANKL to RANK induces the formation, activation, and survival of mature osteoclasts and the stimulation of intracellular signaling cascades leading to increased bone resorption. Neutralizing antibodies to RANKL are known in the art. For example, U.S. Pat. No. 6,740,522 discloses anti-RANKL antibodies including Denosumab, marketed under the name Prolia, which is the only approved anti-RANKL therapeutic antibody (approved for the treatment of osteoporosis in postmenopausal women and men at high risk for fracture).

Parathyroid hormone (PTH) is an eighty-four amino acid peptide which plays a central role in bone remodeling. PTH binding to the PTH receptor 1 directly induces bone formation through activation of cyclic AMP and canonical wnt-signaling pathways. Therapeutic PTH peptides are known in the art. For example, International Patent Publication No. WO/2000/010596 discloses teriparatide (rhPTH(1-34)), a therapeutic PTH peptide marketed as Forteo®. Forteo® PTH peptide is a thirty-four amino acid N-terminal fragment of PTH that has been shown to increase bone formation activity in osteoporotic patients and is the only bone anabolic agent approved in the United States to treat osteoporosis.

Although neutralizing antibodies to RANKL and therapeutic PTH peptides are known, there exists no combined therapy for inhibiting the activity of RANKL and promoting the bone anabolic properties of PTH. Thus, there remains a need for an alternative therapy that combines the bone anabolic properties of PTH with the anti-bone resorptive properties of anti-RANKL for patients having low bone mass disorders such as osteopenia, osteogenesis imperfecta, transplant-associated bone loss, autoimmune-induced bone loss, and/or disuse-induced bone loss and/or to aide in bone healing of disorders such as degenerative lumbar spondylolisthesis or degenerative disk disease as well as bone healing for spinal fusion and fracture patients. One approach to such an alternative therapy may include the co-administration of separate agents, either through administration of separate formulations (each containing a separate active agent), or administration of a single, co-formulation containing each of the individual agents. While two injections permit flexibility of dose amounts and timing, it is inconvenient to patients both for compliance and pain. On the other hand, although a single administration of a co-formulation of multiple agents could provide convenience, it is often quite challenging or impossible to find formulation conditions achieving the necessary chemical and physical stability as well as bioavailability of each agent. Additionally, both co-administration and co-formulation involve the additive development, manufacturing, and regulatory costs associated with each agent.

The present invention addresses the need for an alternative therapy for patients having bone disorders, and more particularly having low bone mass disorders such as osteoporosis. In further embodiments, the bone disorder is one or more of osteopenia, osteogenesis imperfecta, transplant-associated bone loss, autoimmune-induced bone loss disuse-induced bone loss, degenerative lumbar spondylolisthesis and/or degenerative disk disease. More particularly, the present invention provides fusion compounds capable of inhibiting the activity of RANKL and promoting the bone anabolic properties of PTH. The fusion compounds of the present invention provide a pharmaceutical agent suitable for systemic administration and which may also be useful as agents for bone healing, for example in treating fractures and other conditions associated with, or resulting from, bone disorders, including bone mass loss or degeneration.

The present invention provides compounds, more specifically fusion compounds, having a first polypeptide and a second polypeptide. The first polypeptide has a parathyroid hormone (PTH) peptide and a mAb IgG heavy chain (HC), with the PTH peptide having an amino acid sequence given by SEQ ID NO: 13, and the HC having a heavy chain variable region (HCVR) comprising heavy chain complementary determining regions (HCDR) 1-3, where HCDR1 has the amino acid sequence given by SEQ ID NO: 7, HCDR2 has the amino acid sequence given by SEQ ID NO:

8, and HCDR3 has the amino acid sequence given by SEQ ID NO: 9. The second polypeptide has a mAb light chain (LC) having a light chain variable region (LCVR) comprising light chain complementary determining regions (LCDR) 1-3, where LCDR1 has the amino acid sequence given by SEQ ID NO: 10, LCDR2 has the amino acid sequence given by SEQ ID NO: 11, and LCDR3 has the amino acid sequence given by SEQ ID NO: 12. According to such compounds, the PTH peptide is linked to the HC via a polypeptide linker (L1), L1 being covalently attached to the N-terminus of HC and the C-terminus of the PTH peptide.

In some particular embodiments, the present invention provides compounds in which the HCVR has an amino acid sequence given by SEQ ID NO: 5 and the LCVR has an amino acid sequence given by SEQ ID NO: 6. In some more specific embodiments, the present invention provides compounds in which the first polypeptide has an amino acid sequence given by SEQ ID NO: 1 and the second polypeptide has an amino acid sequence given by SEQ ID NO: 2. In further embodiments, the present invention includes compounds in which L1 has an amino acid sequence given by SEQ ID NO: 14. In even further embodiments, the compounds of the present invention comprise two first polypeptides and two second polypeptides.

The present invention also relates to nucleic acid molecules and expression vectors encoding the fusion compounds of the present invention. In an embodiment, the present invention provides a DNA molecule comprising a polynucleotide sequence encoding the first polypeptide chain, wherein the amino acid sequence of the first polypeptide chain is SEQ ID NO: 1. According to some such embodiments, the DNA molecule has a polynucleotide sequence given by the SEQ ID NO: 3.

In an embodiment, the present invention also provides a DNA molecule comprising a polynucleotide sequence encoding the second polypeptide chain, wherein the amino acid sequence of the second polypeptide chain is SEQ ID NO: 2. According to some such embodiments, the DNA molecule has a polynucleotide sequence given by the SEQ ID NO: 4.

In a further embodiment, the present invention provides a DNA molecule comprising a polynucleotide sequence encoding the first polypeptide chain having the amino acid sequence of SEQ ID NO: 1, and comprising a polynucleotide sequence encoding the second polypeptide chain having the amino acid sequence of SEQ ID NO: 2. In a particular embodiment the polynucleotide sequence encoding the first polypeptide chain having the amino acid sequence of SEQ ID NO: 1 is given by SEQ ID NO: 3 and the polynucleotide sequence encoding the second polypeptide chain having the amino acid sequence of SEQ ID NO: 2 is given by SEQ ID NO: 4.

The present invention also provides a mammalian cell transformed with DNA molecule(s) which cell is capable of expressing a compound comprising the first polypeptide and the second polypeptide of the present invention, wherein the first polypeptide has an amino acid sequence given by SEQ ID NO: 1 and the second polypeptide has an amino acid sequence given by SEQ ID NO: 2. Also, the present invention provides a process for producing a compound comprising the first polypeptide and the second polypeptide, comprising cultivating the mammalian cell under conditions such that the compound of the present invention is expressed. The present invention also provides a compound produced by said process.

The present invention also provides a pharmaceutical composition comprising a compound of the present invention and one or more pharmaceutically acceptable carriers, diluents, or excipients. Pharmaceutical compositions of the present invention can be used in the treatment of a bone disorder, whereby such treatment comprises administering to a patient in need thereof a therapeutically effective amount of a pharmaceutical composition of the present invention. In some embodiments, the bone disorder is one or more of osteoporosis, osteopenia, osteogenesis imperfecta, transplant-associated bone loss, autoimmune-induced bone loss, and/or disuse-induced bone loss. In some embodiments, the bone disorder is one or more of degenerative lumbar spondylolisthesis and/or degenerative disk disease.

The present invention also provides a method of treating a bone disorder comprising administering to a patient in need thereof a therapeutically effective amount of a compound of the present invention. In some such embodiments the bone disorder is osteoporosis. In further embodiments, the bone disorder is one or more of osteopenia, osteogenesis imperfecta, transplant-associated bone loss, autoimmune-induced bone loss, and/or disuse-induced bone loss. In further embodiments, the bone disorder is one or more of degenerative lumbar spondylolisthesis and/or degenerative disk disease. In even further embodiments, the present invention provides a method of treating a spinal fusion patient and/or a bone fracture patient.

The present invention also provides a compound of the present invention or pharmaceutical composition thereof for use in therapy. More particularly, the present invention provides a compound of the present invention or pharmaceutical composition thereof for use in the treatment of a bone disorder and/or bone healing, wherein the bone disorder is one or more of osteoporosis, osteopenia, osteogenesis imperfecta, transplant-associated bone loss, autoimmune-induced bone loss, disuse-induced bone loss, degenerative lumbar spondylolisthesis, and/or degenerative disk disease.

In an embodiment, the present invention also provides the use of a compound of the present invention or a pharmaceutical composition thereof in the manufacture of a medicament for the treatment of a bone disorder and/or bone healing. According to particular embodiments, the present invention provides a compound of the present invention or pharmaceutical composition thereof in the manufacture of a medicament for the treatment of at least one of or more of osteoporosis, osteopenia, osteogenesis imperfecta, transplant-associated bone loss, autoimmune-induced bone loss, disuse-induced bone loss, degenerative lumbar spondylolisthesis, and/or degenerative disk disease.

As referred to herein, when describing the instant invention the terms "compound" and "fusion compound" are used interchangeably. The fusion compounds of the present invention are bifunctional, meaning they are capable of interacting with, and modulating the activity of, two distinct targets. Specifically, the fusion compounds of the present invention are agonists of the human PTH receptor and also interact with and inhibit the activity of human RANKL. In combining an agonist of the human PTH receptor and a RANKL antibody into a single compound, it is believed the fusion compounds of the present invention will demonstrate bone formation and/or anti-bone resorptive effects in patients. Thus, the compounds of the present invention, or pharmaceutical compositions thereof, may be useful in the treatment of bone healing and/or low bone mass disorders; for example osteoporosis, osteopenia, osteogenesis imperfecta, transplant-associated bone loss, autoimmune-induced bone loss, disuse-induced bone loss, degenerative lumbar spondylolisthesis, degenerative disk disease, bone fractures, and/or spinal fusion patients.

Also, compounds of the present invention comprise four polypeptide chains, two first polypeptides and two second polypeptides. As represented in the following schematic, each of the first polypeptides is engineered to comprise a parathyroid hormone (PTH) peptide linked at the N-terminus of a mAb heavy chain (HC) by a polypeptide linker (L1). Linker L1 is typically of about 10 to 25 amino acids in length and rich in one or more of glycine, serine, or threonine amino acids. Each of the second polypeptide chains is engineered to comprise a mAb light chain (LC) and form inter-chain disulfide bonds with one of the first polypeptide, specifically within the HC of a first polypeptide. Each first polypeptide is engineered to form inter-chain disulfide bonds with the other first polypeptide, specifically between the HC of each of the first polypeptides.

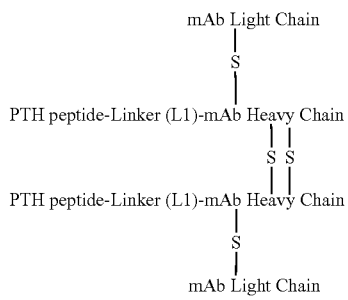

The polypeptide chains of the compounds of the present invention are depicted by their sequence of amino acids from N-terminus to C-terminus, when read from left to right, with each amino acid represented by either its single letter or three-letter amino acid abbreviation. Unless otherwise stated herein, all amino acids used in the preparation of the polypeptides of the present invention are L-amino acids. The "N-terminus" (or amino terminus) of an amino acid, or a polypeptide chain, refers to the free amine group on the amino acid, or the free amine group on the first amino acid residue of the polypeptide chain. Likewise, the "C-terminus" (or carboxy terminus) of an amino acid, or a polypeptide chain, refers to the free carboxy group on the amino acid, or the free carboxy group on the final amino acid residue of the polypeptide chain.

According to compounds of the present invention, the HC of each first polypeptide is classified as gamma, which defines the isotype (e.g., as an IgG). The isotype may be further divided into subclasses (e.g., $IgG_1$, $IgG_2$, $IgG_3$, and $IgG_4$). In particular embodiments, compounds of the present invention comprise mAb heavy chains (HCs) of the IgG4 type. Each HC is comprised of an N-terminal heavy chain variable region (HCVR) followed by a constant region (CH), comprised of three domains ($C_H1$, $C_H2$, and $C_H3$) and a hinge region.

Additionally, according to compounds of the present invention each mAb light chain (LC) is classified as kappa or lambda and characterized by a particular constant region as known in the art. In particular embodiments the compounds of the present invention comprise kappa LCs. Each LC is comprised of an N-terminal light chain variable region (LCVR) followed by a light chain constant region (CL).

The HCVR and LCVR, of each HC and LC respectively, can be further subdivided into regions of hypervariability, termed complementarity determining regions (CDRs), interspersed with regions that are more conserved, termed framework regions (FR). Preferably, the framework regions of compounds of the present invention are of human origin or substantially of human origin. Each HCVR and LCVR of compounds according to the present invention are composed of three CDRs and four FRs, arranged from amino-terminus to carboxy-terminus in the following order: FR1, CDR1, FR2, CDR2, FR3, CDR3, FR4. Herein the 3 CDRs of each HCVR are referred to as "HCDR1, HCDR2, and HCDR3" and the 3 CDRs of each LCVR are referred to as "LCDR1, LCDR2, and LCDR3." The CDRs contain most of the residues which form specific interactions with the antigen. The functional ability of a compound of the present invention to bind a particular antigen, e.g., RANKL, is largely influenced by the CDRs.

As used interchangeably herein, "antigen-binding site" and "antigen-binding region" refers to the portion(s) of compounds of the present invention which contain the amino acid residues that interact with an antigen and confer to the compound specificity and affinity for a respective antigen. According to compounds of the present invention, antigen-binding sites are formed by a HCVR/LCVR pair (of a LC and HC bound by inter-chain disulfide bonds). Additionally, according to compounds of the present invention, antigen-binding sites formed by each HCVR/LCVR pair are the same (e.g., comprises affinity for a same antigen, RANKL).

The terms "Kabat numbering" or "Kabat labeling" are used interchangeably herein. These terms, which are recognized in the art, refer to a system of numbering amino acid residues which are more variable (i.e., hypervariable) than other amino acid residues in the heavy chain and light chain variable regions of an antibody (Kabat, et al., *Ann. NY Acad. Sci.* 190:382-93 (1971); Kabat et al., *Sequences of Proteins of Immunological Interest*, Fifth Edition, U.S. Department of Health and Human Services, NIH Publication No. 91-3242 (1991)).

The terms "North numbering" or "North labeling" are used interchangeably herein. These terms, which are recognized in the art, refer to a system of numbering amino acid residues which are more variable (i.e., hypervariable) than other amino acid residues in the heavy and light chains variable regions of an antibody and is based, at least in part, on affinity propagation clustering with a large number of crystal structures, as described in North et al., *A New Clustering of Antibody CDR Loop Conformations*, Journal of Molecular Biology, 406:228-256 (2011).

Fusion Compound Engineering

Significant issues were encountered when attempting to construct a fusion compound of the present invention. Problems encountered included engineering a single agent which possesses compatible and/or optimal bioactivity for both an increase in bone formation and a decrease in bone resorption. For example, a fusion compound comprising a PTH peptide (e.g., such as is described in International Patent Publication No. WO/2000/010596) linked with a known RANKL antibody (e.g., Denosumab, such as described in U.S. Pat. No. 6,740,522) does not provide an agent having compatible and/or acceptable bioactivity. It is known that Denosumab possesses a half life (for decreasing bone resorption) of approximately greater than 25 days when injected subcutaneously, whereas the half life of teriparatide (for increasing bone formation) is approximately 1 hour when injected subcutaneously. Such disparate biological activity profiles create an issue for dosing, in which delivering a therapeutic effective amount must be balanced with risks of both acute hypercalcemia and longer-term hypocalcemia. Additionally, sustained exposure to PTH can lead to undesirable catabolic bone loss and thus dosing of PTH with known RANKL antibodies is an issue. As such, in order to arrive at a fusion compound enabling dosing of therapeutically effective amounts of a PTH peptide and a RANKL antibody which also balances the potential side effects (e.g., acute hypercalcemia, longer-term hypocalcemia, and catabolic bone loss), pharmacological intervention is needed.

As a result of the significant issues detailed above relating to engineering a fusion compound of the present invention, in order to arrive at a therapeutic fusion compound possessing a bioactivity profile acceptable for use in the treatment of low bone mass disorders and bone healing, a novel RANKL antibody was developed and engineered. As such, a fusion compound comprising a PTH portion (teriparatide) linked with a novel RANKL mAb portion (described in further detail herein) was engineered. The engineered fusion compounds of the present invention comprise therapeutically acceptable and compatible bioactivity profiles for bone resorption (decrease) and bone formation (increase) for use in the treatment of low bone mass disorders and bone healing.

Additional problems encountered when attempting to construct a fusion compound of the present invention included compound aggregation in solution, clipping of the PTH peptide portion from the RANKL mAb portion, and reduced binding of the RANKL mAb portion. For example, initial attempts in constructing a fusion compound according to the present invention included constructs utilizing a PTH peptide having the native 84 amino acid sequence given by SEQ ID NO: 15, and fragments of varying lengths (of the N-terminus region thereof) linked to various RANKL antibodies (e.g., known RANKL antibodies such as Denosumab and novel RANKL antibody constructs). Initial constructs also included the PTH peptide linked to the RANKL mAb portion in various configurations including at the N-terminus or the C-terminus for both the heavy and light chains, respectively. Some constructs included the PTH peptide portion being linked to the RANKL antibody portion with no linker as well as amino acid linkers of varying structure and size. Initial attempted fusion compound constructs exhibited one or more of the chemical and/or physical issues described above. However, the engineered fusion compounds of the present invention surprisingly and unexpectedly resulted in a compound possessing therapeutically acceptable expression, stability, and affinity. None of the modifications resulting in the fusion compounds of the present invention are routine or common general knowledge suggested or taught in the art.

Fusion Compound Expression

Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. Each of the first polypeptides and the second polypeptides may be expressed independently from different promoters to which they are operably linked in one vector or, alternatively, the first and second polypeptides may be expressed independently from different promoters to which they are operably linked in two vectors—one expressing the first polypeptide and one expressing the second polypeptide. Exemplary suitable vectors for use in preparing fusion compounds of the present invention include vectors available from Lonza Biologics such as pEE 6.4 (for expressing the first polynucleotide sequence for example) and pEE 12.4 (for expressing the second polynucleotide sequence for example).

A particular DNA polynucleotide sequence encoding an exemplified first polypeptide (comprising a PTH peptide linked at the N-terminus of a HC via a flexible glycine serine linker) of a fusion compound of the present invention having the amino acid sequence of SEQ ID NO: 1 is provided by SEQ ID NO: 3 (the DNA polynucleotide sequence provided by SEQ ID NO: 3 also encodes a signal peptide). A particular DNA polynucleotide sequence encoding an exemplified second polypeptide (comprising a LC) of a fusion compound of the present invention having the amino acid sequence of SEQ ID NO: 2 is provided by SEQ ID NO: 4 (the DNA polynucleotide sequence provided by SEQ ID NO: 4 also encodes a signal peptide).

A host cell includes cells stably or transiently transfected, transformed, transduced, or infected with one or more expression vectors expressing a first polypeptide, a second polypeptide or both a first and a second polypeptide of the present invention. Creation and isolation of host cell lines producing a fusion compound of the present invention can be accomplished using standard techniques known in the art. Mammalian cells are preferred host cells for expression of fusion compounds of the present invention. Particular mammalian cells are CHO, NS0, and DG-44. Preferably, the fusion compounds are secreted into the medium in which the host cells are cultured, from which the fusion compounds can be recovered or purified by conventional techniques. For example, the medium may be applied to and eluted from a Protein A or G affinity chromatography column and size exclusion or CAPTO™ multimodal chromatography using conventional methods. Additionally, soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

Therapeutic Uses

As used herein, "treatment" and/or "treating" are intended to refer to all processes wherein there may be a slowing, interrupting, arresting, controlling, or stopping of the progression of the disorders described herein (for example, bone mass loss such as associated with osteoporosis, or a disorder impeding bone healing), but does not necessarily indicate a total elimination of all disorder symptoms. Treatment includes administration of a compound of the present invention, or pharmaceutical composition thereof, for treatment of a disease or condition in a patient that would benefit from the bone anabolic properties of PTH and a decreased level of RANKL or decreased bioactivity of RANKL. Treatment includes: (a) inhibiting further progression of the disease, i.e., arresting bone mass loss and/or a barrier to bone healing; and (b) relieving the disease, i.e., causing regression of the disease or disorder or alleviating symptoms or complications thereof causing bone mass loss and/or inhibiting bone healing. Compounds of the present invention are expected to be useful in the treatment of one or more of bone disease, for example in bone mass loss disease such as osteoporosis, osteopenia, osteogenesis imperfecta, transplant-associated bone loss, autoimmune-induced bone loss, and/or disuse-induced bone loss, and/or in bone healing of disorders such as degenerative lumbar spondylolisthesis and/or degenerative disk disease as well as in bone healing for bone fracture and spinal fusion patients.

The terms "patient," "subject," and "individual," used interchangeably herein, refer to a human. In some embodiments, a patient is a human that has been diagnosed as "in need of" or being "at risk of" needing or in need of treatment for a bone disorder, bone healing, for example fracture repair, prevention of bone loss or degeneration, and/or as being at risk of developing or in need of treatment for osteoporosis, osteopenia, osteogenesis imperfecta, transplant-associated bone loss, autoimmune-induced bone loss, and/or disuse-induced bone loss.

Pharmaceutical Composition

Compounds of the present invention can be incorporated into a pharmaceutical composition suitable for administration to a patient. The compounds of the present invention are intended for administration via parental routes including, intravenous, intramuscular, subcutaneous, or intraperitoneal. Additionally, compounds of the present invention may be administered to a patient alone or with a pharmaceutically acceptable carrier and/or diluent in single or multiple doses. Such pharmaceutical compositions are designed to be appropriate for the selected mode of administration, and pharmaceutically acceptable diluents, carriers, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., *Remington, The Science and Practice of Pharmacy*, 19$^{th}$ Edition, Gennaro, Ed., Mack Publishing Co., Easton, Pa. 1995 which provides a compendium of formulation techniques as are generally known to practitioners. Suitable carriers for pharmaceutical compositions include any material which, when combined with a compound of the present invention, retains the molecule's activity and is non-reactive with the patient's immune system. A pharmaceutical composition of the present invention comprises a compound and one or more pharmaceutically acceptable carriers, diluents, or excipients.

An effective amount of a compound of the present invention refers to an amount necessary (at dosages and for periods of time and for the means of administration) to achieve the desired therapeutic result. An effective amount of the compound or pharmaceutical composition thereof may vary according to factors such as the disease state, age, sex, and weight of the individual, and the ability of the compound or portion(s) thereof to elicit a desired response in the individual. An effective amount is also one in which any toxic or detrimental effect of the compound is outweighed by the therapeutically beneficial effects.

EXAMPLES

Fusion Compound Expression and Purification

An exemplified fusion compound of the present invention is expressed and purified essentially as follows. A glutamine synthetase (GS) expression vector containing the polynucleotide sequences given by SEQ ID NO: 3 (encoding an exemplified first polypeptide of SEQ ID NO: 1 and a post-translationally cleaved signal peptide) and SEQ ID NO: 4 (encoding an exemplified second polypeptide of SEQ ID NO: 2 and a post-translationally cleaved signal peptide) is used to transfect a Chinese hamster cell line (CHO, GS knockout), by electroporation. The expression vector encodes a SV Early (Simian Virus 40E) promoter and the gene for GS. Expression of GS allows for the biochemical synthesis of glutamine, an amino acid required by the CHO cells. Post-transfection, cells undergo bulk selection with 50 µM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells. Transfected pools are plated at low density to allow for close-to-clonal outgrowth of stable expressing cells. The master-wells are screened for fusion compound expression and then scaled up in serum-free, suspension cultures to be used for production.

Clarified medium, into which the exemplified compound has been secreted, is applied to a Protein A affinity column that has been equilibrated with a compatible buffer such as phosphate buffered saline (pH 7.4). The column is washed to remove nonspecific binding components. The bound fusion compound is eluted, for example, by pH gradient and neutralized for example with Tris, pH 8 buffer. Fusion compound fractions are detected, such as by SDS-PAGE or analytical size-exclusion, and then are pooled. Soluble aggregate and multimers may be effectively removed by common techniques including size exclusion, hydrophobic interaction, CAPTO™ multimodal chromatography, ion exchange, or hydroxyapatite chromatography. The fusion compound is concentrated and/or sterile filtered using common techniques. The purity of the exemplified fusion compound after these chromatography steps is greater than 98% (monomer). The fusion compound may be immediately frozen at −70° C. or stored at 4° C. for several months.

The relationship of the various regions and linkers comprising an exemplified fusion compound of the present invention, expressed and purified following procedures essentially as described above, is presented in Table 1 (numbering of amino acids applies linear numbering; assignment of amino acids to variable domains is based on the International Immunogenetics Information System® available at www.imgt.org; assignment of amino acids to CDR domains is based on the well-known Kabat and North numbering conventions as reflected at the end of Table 1):

TABLE 1

Amino acid regions of an exemplified fusion compound of the present invention.

| SEQ ID NO: 1 | | | SEQ ID NO: 2 | | |
| --- | --- | --- | --- | --- | --- |
| Portion | Region | A.A. Pos. | Portion | Region | A.A. Pos. |
| Exemplified PTH Peptide | PTH Peptide | 1-34 | | | |
| Exemplified Linker | L1 | 35-49 | | | |
| Exemplified RANKL HCVR | FRH1 | 50-74 | Exemplified RANKL LCVR | FRL1-1 | 1-23 |
| | HCDR1 | 75-84 | | LCDR1 | 24-34 |
| | FRH2 | 85-98 | | FRL1-2 | 35-49 |
| | HCDR2 | 99-115 | | LCDR2 | 50-56 |
| | FRH3 | 116-147 | | FRL1-3 | 57-88 |
| | HCDR3 | 148-159 | | LCDR3 | 89-97 |
| | FRH4 | 160-170 | | FRL1-4 | 98-107 |
| HC Constant Region | CH | 171-496 | LC Constant Region | CL | 108-214 |

| CDR | Starting Amino Acid Residue Defined By: | Ending Amino Acid Residue Defined By: |
| --- | --- | --- |
| HCDR1 | North | Kabat |
| HCDR2 | Kabat | Kabat |
| HCDR3 | North | Kabat |
| LCDR1 | Kabat | Kabat |
| LCDR2 | North | Kabat |
| LCDR3 | Kabat | Kabat |

The exemplified compound presented in Table 1 comprises two first polypeptides having amino acid sequences of SEQ ID NO: 1 and two second polypeptides having amino acid sequences of SEQ ID NO: 2. According to the exemplified fusion compound, each of the first polypeptides forms an inter-chain disulfide bond with each of the second polypeptides between cysteine residue 184 of SEQ ID NO: 1 and cysteine residue 214 of SEQ ID NO: 2; at least two inter-chain disulfide bonds with the other first polypeptide, the first inter-chain disulfide bond forming between cysteine residue 276 (of SEQ ID NO: 1) of the first polypeptide and cysteine residue 276 (of SEQ ID NO: 1) of the other first polypeptide, the second inter-chain disulfide bond forming between cysteine residue 279 (of SEQ ID NO: 1) of the first polypeptide and cysteine residue 279 (of SEQ ID NO: 1) of the other first polypeptide. Further, the exemplified compound presented in Table 1 is glycosylated at asparagine residue 347 of SEQ ID NO: 1 of both first polypeptides.

Except as noted otherwise herein, the exemplified fusion compound referred to throughout the Examples refers to the exemplified compound of the present invention presented in Table 1.

Fusion Compound Binding Affinity to RANKL

Binding affinity and binding stoichiometry of the exemplified fusion compound to human and murine RANKL is determined using a surface plasmon resonance assay on a BIACORE 2000™ instrument primed with HBS-EP+ (10 mM Hepes, pH7.4+150 mM NaCl+3 mM EDTA+0.05% (w/v) surfactant P20) running buffer and analysis temperature set at 25° C. A CM5 chip (Biacore, p/n.BR-100530) containing immobilized protein A (generated using standard NHS-EDC amine coupling) on all four flow cells (Fc) is used to employ a capture methodology. Fusion compound samples are prepared at 2 µg/mL by dilution into running buffer. Human and murine RANKL samples, respectively, are prepared at final concentrations starting at 5 nM and using two-fold serial dilutions (in running buffer) for each cycle.

Each analysis cycle consists of (1) capturing antibody samples on separate flow cells (Fc2 and Fc3); (2) injection of each human and murine RANKL concentration, respectively, over all Fc at 100 µL/min for 150 seconds followed by return to buffer flow for 1800 seconds to monitor dissociation phase; (3) regeneration of chip surfaces with injection of 10 mM glycine, pH 1.5, for 120 seconds at 5 µL/min over all cells; and (5) equilibration of chip surfaces with a 10 µL (60-sec) injection of HBS-EP+. Data are processed using standard double-referencing and fit to a 1:1 binding model using BIACORE 2000™ Evaluation software, version 2.0.3, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) is calculated from the relationship $K_D=k_{off}/k_{on}$, and is in molar units. Results are provided in Table 2.

TABLE 2

Binding affinity to human and murine RANKL by the exemplified fusion compound.

| Antigen | $k_{on}$ Avg. ($10^7$ $M^{-1}s^{-1}$) | $k_{off}$ Avg. $s^{-1}$ ($10^{-5}$) | $K_D$ Avg. pM | n |
|---|---|---|---|---|
| Human RANKL | 0.35 | 1.69 | 4.82 | 4 |
| Murine RANKL | 1.16 | 9.69 | 8.37 | 1 |

The results provided in Table 2 demonstrate that the exemplified fusion compound of the present invention binds human and murine RANKL with high affinity at 25° C.

Neutralization of RANKL-Induced NF-kB-Driven Luciferase Activity In Vitro

HEK293 cells, which stably co-express human RANK and a NF-kB driven luciferase reporter, are used to assess the ability of the exemplified fusion compound presented in Table 1 to neutralize RANKL activity. In the above-described HEK293 cell model, RANK, when bound by human RANKL, induces NF-kB signaling resulting in luciferase luminescence. Neutralization of RANKL binding to RANK, by the exemplified fusion compound, is measured by a reduction of luciferase luminescence.

HEK293 cells are routinely cultured under selective pressure of 700 µg/mL Geneticin (HyClone, p/n.SV30069.01). 25,000 cells/well are added to the wells of 96 well tissue culture plates (Benton Dickinson, p/n.354620) in assay media (504, DMEM/F12 (1:3) media (Gibco, p/n.930152DK) containing 0.5% FBS (Gibco, p/n.10082-147), 20 nM Hepes (HyClone, p/n.SH30237.01), 1×GlutaMax GLUTAMAX™ media supplement (Gibco, p/n.35050-61) and 1× penicillin/streptomycin (Hyclone, p/n.SV30010)). Cells are incubated at 37° C. (with 5% $CO_2$ and 95% humidity) overnight.

Assay media including 1 nM and 10 nM concentrations of human RANKL are used to prepare dose ranges of 10 nM to 0.005 nM (with 1:3 serial dilutions) for each of: a.) the exemplified fusion compound; and b.) a RANKL neutralizing antibody (an IgG4 RANKL mAb having the same HC and LC amino acid sequences as the mAb portion of the exemplified fusion compound). Assay medium is used for a "media only" control. All treatment groups are incubated for 15 minutes at room temperature. Thereafter, 50 µl of each treatment group is added to 50 µl of media containing cultured cells. The mixture of treatment group and cultured cells are incubated overnight at 37° C.

Following overnight incubation existing growth media is removed and cells are suspended in 504, of BUGLITE™ solution (2.296 g DTT (Sigma, p/n.D0632), 1.152 g Coenzyme A (Sigma, p/n. C-3019), 0.248 g ATP (Sigma, p/n.A7699) in 1 L 1% TRITON X-100™ Lysis Buffer (30 mL TRITON X-100™ (Fisher, p/n.BP151-500), 3 mL MgCl (Sigma, p/n.M9272), 108.15 mL 1M TRIZMA™ HCL (Sigma, p/n.T-3253), 41.85 mL 1M TRIZMA™ Base (Sigma, p/n.T-1503) and 817 mL H2O)). Cells are then lysed with gentle agitation on a plate shaker for between 5 to 10 minutes. Following cell lysis, luminescence is measured on a plate reader (Envision Plate Reader). $IC_{50}$ values for all treatment groups are calculated using a three-parameter logistic regression model with GraphPad Prism 6 and are presented in Table 3.

TABLE 3

Neutralization of human RANKL by the exemplified fusion compound.

| Molecule | IC50 (nM) hRANKL | n |
|---|---|---|
| Exemplified Fusion Compound | 0.067 | 11 |
| RANKL mAb | 0.069 | 3 |

The results presented in Table 3 demonstrate that the exemplified fusion compound of the present invention neutralizes human RANKL induced NF-kB driven luciferase luminescence. The inhibition was comparable to that observed with the positive control RANKL antibody. Media controls did not neutralize human RANKL induced NF-kB driven luciferase luminescence in the HEK293 cell model at any concentration tested. These results demonstrate the exemplified fusion compound of the present invention effectively neutralizes RANKL.

Activation of PTHR1 Receptor-Induced Luciferase Activity In Vitro

Rat osteosarcoma UMR-106 cells (ATCC, p/n.CRL-1661) which endogenously express PTH receptor and which have been stably co-transfected (using Roche Fugene6 reagent) with a pTranslucent CRE(1) Luciferase Reporter Vector (Panomics, p/n. LR0093) and pEGFP-N1 (Clontech), are used to assess the ability of the exemplified fusion compound presented in Table 1 to activate the PTHR1 receptor. PTH binding of the PTH receptor (expressed by the UMR-106 cells) induces CRE-regulated luciferase luminescence. Activation of the PTHR1 receptor by the exemplified fusion compound is measured through quantification of luciferase luminescence.

The co-transfected UMR-106 cells are grown at 37° C. and 10% $CO_2$ in DMEM/HEPES, 10% FBS, 1× Penicillin, Streptomycin, and Glutamine, and 2 mg/ml G418. UMR-106 cells (at a concentration of 50,000 cells/well) are added to an opaque white plate and incubated overnight at 37° C. (under 10% $CO_2$). Following incubation, a dose range of 0 nM to 1250 nM of one of a.) the exemplified fusion compound; b.) a RANKL neutralizing antibody (an IgG4 RANKL mAb having the same HC and LC amino acid sequences as the mAb portion of the exemplified fusion compound) and c.) a PTH peptide (a 38 amino acid parathyroid hormone peptide) is added to the seeded plates and plates are incubated at 37° C. (under 10% $CO_2$) for four to six hours. Thereafter, 50 µL of BugLite is added to each plate and luminescence is measured on a plate reader (Envision Plate Reader). $EC_{50}$ values for all treatment groups are calculated using a three-parameter logistic regression model with GraphPad Prism or JMP and are presented in Table 4.

TABLE 4

PTHR1 Activation by the exemplified fusion compound.

| Molecule | EC50 (nM) | n |
| --- | --- | --- |
| Exemplified Fusion Compound | 6.6 | 10 |
| RANKL mAb | 0.0 | 10 |
| PTH Peptide | 5.6 | 5 |

The results presented in Table 4 demonstrate that the exemplified fusion compound of the present invention both binds PTHR1 receptor and activates the downstream PTHR1 signaling cascade in vitro. As the results demonstrate, the ability of the exemplified fusion compound to activate PTHR1 signaling compares favorably with the PTH peptide alone.

In Vivo Efficacy Analysis in Intact Murine Model

Effects on bone mass density, in vivo, are assessed using an intact female murine model. C57/B6 intact female mice, aged twenty to twenty-two weeks (Charles River) are maintained on a 12 hour light/dark cycle at 22° C. with ad lib access to food (TD 2014 with 0.72% Ca and 0.61% P, Vit. D 0.99 IU/g, Teklad, Madison, Wis.) and water.

The mice are divided into treatment groups or a PBS vehicle control group. Each treatment group of mice receives a weekly subcutaneous injection of one of: a.) 3 mg/kg or 10 mg/kg exemplified fusion compound; b.) 10 mg/kg RANKL neutralizing antibody (an IgG4 RANKL mAb having the same HC and LC amino acid sequences as the mAb portion of the exemplified fusion compound); or c.) co-administration of 10 mg/kg of the RANKL neutralizing antibody and 3 mg/kg PTH peptide (a 38 amino acid parathyroid hormone peptide). Mice are sacrificed at four weeks.

Bone mass density (BMD) of distal and mid-femur is monitored by quantitative computed tomography (qCT) using Aloka LaTheta LTC-100 model CT scanner. Results are provided in Table 5 (data presented as mean % difference compared to vehicle control using Dunnett's Method with a significance level of $P<0.05$).

TABLE 5

Skeletal BMD Analysis.

| | % BMD Increase Over Vehicle Control Mice | | |
| --- | --- | --- | --- |
| | Distal-Femur | Middle-Femur | n |
| Exemplified fusion compound (3 mg/kg) | 31 | 12 | 6 |
| Exemplified fusion compound (10 mg/kg) | 55 | 14 | 6 |
| Rank mAb Alone (10 mg/kg) | 23 | 4 | 6 |
| Rank mAb (10 mg/kg) + PTH peptide (3 µg/kg) | 17 | 9 | 6 |

The results presented in Table 5 demonstrate that, dosed weekly, the exemplified fusion compound of the present invention demonstrates a dose-dependent increase of BMD at both the distal and middle femur over RANKL antibody only treated mice and co-administration of RANKL antibody and PTH peptide treated mice.

In Vivo Efficacy Analysis in Ovariectomized Murine Model

Effects on bone mass density, in vivo, are assessed using an ovariectomized murine model. Twenty week old female C57/B6 mice (Harlan, Indianapolis, Ind.) are ovariectomized (or sham operated control group) and maintained on a 12 hour light/dark cycle at 22° C. with ad lib access to food (TD 2014 with 0.72% Ca and 0.61% P, Vit. D 0.99 IU/g, Teklad, Madison, Wis.) and water. Osteopenia is established in the mice by allowing ovariectomized mice to lose bone mass for a six-week period.

Following a six-week osteopenia-establishing period, mice are divided into treatment groups or a vehicle PBS control group. Each treatment group of mice receives a weekly subcutaneous injection of one of: a.) 1 mg/kg or 3 mg/kg exemplified fusion compound; b.) 3 mg/kg or 10 mg/kg RANKL neutralizing antibody (an IgG4 RANKL mAb having the same HC and LC amino acid sequences as the mAb portion of the exemplified fusion compound); or c.) co-administration of 10 mg/kg of the RANKL neutralizing antibody and 10 mg/kg PTH peptide (a 38 amino acid parathyroid hormone peptide). Mice are sacrificed at four weeks.

Skeletal bone mass density (BMD) of vertebrae 5 is assessed by quantitative computed tomography (qCT), using Aloka LaTheta LTC-100 model CT scanner, following sacrifice. Results are provided in Table 6 (data presented as mean % difference compared to sham-operated control group using Dunnett's Method with a significance level of $P<0.05$).

TABLE 6

Skeletal BMD Analysis.

| Molecule | % BMD Increase Over OVX vehicle control Mice | n |
|---|---|---|
| Exemplified fusion compound (1 mg/kg) | 11 | 6 |
| Exemplified fusion compound (3 mg/kg) | 19 | 6 |
| Rank mAb Alone (3 mg/kg) | 2 | 6 |
| Rank mAb Alone (10 mg/kg) | 11 | 6 |
| Rank mAb (10 mg/kg) + PTH peptide (10 µg/kg) | 13 | 6 |

The results presented in Table 6 demonstrate that, dosed weekly, the exemplified fusion compound of the present invention demonstrates a dose-dependent increase of bone mass density of vertebrae over RANKL antibody only treated mice and co-administration of RANKL antibody and PTH peptide treated mice.

In Vivo Efficacy Analysis in Orchidectomized Murine Model

Effects on bone mass density and bone mineral content, in vivo, are assessed using an orchidectomized murine model. Sixteen week old female C57/B6 mice (Harlan, Indianapolis, Ind.) are orchidectomized (or vehicle control group, n=6) and maintained on a 12 hour light/dark cycle at 22° C. with ad lib access to food (TD 2014 with 0.72% Ca and 0.61% P, Vit. D 0.99 IU/g, Teklad, Madison, Wis.) and water. Osteopenia is established in the orchidectomized mice by allowing mice to lose bone mass for a six-week period.

Following a six-week osteopenia-establishing period, mice are divided into treatment groups and a vehicle PBS control group. Each treatment group of mice receives, either weekly or twice-per week (as outlined in Table 7 below), a subcutaneous injection of one of: a.) 0.5 mg/kg or 2.0 mg/kg exemplified fusion compound per week; b.) 0.5 mg/kg or 2.0 mg/kg exemplified fusion compound twice-per week; c.) 2 mg/kg RANKL neutralizing antibody (an IgG4 RANKL mAb having the same HC and LC amino acid sequences as the mAb portion of the exemplified fusion compound) twice-per week; d.) 5 µg/kg PTH peptide (a 38 amino acid parathyroid hormone peptide) daily; or e.) co-administration of 2 mg/kg of the RANKL neutralizing antibody twice-per week and 5 mg/kg PTH peptide daily. Mice are sacrificed at two weeks.

Bone mass density (BMD) of distal femur and bone mineral content (BMC) of lumbar vertebra are assessed by quantitative computed tomography (qCT) using Aloka LaTheta LTC-100 model CT scanner. Results are provided in Table 7 (data presented as mean % difference compared to vehicle control mice using Dunnett's Method with a significance level of P<0.05).

TABLE 7

Skeletal BMD and BMC Analysis (results presented as percent change from vehicle control mice).

| Molecule | n | Dosing Regimen | Distal-Femur (% BMD change) | Lumbar Vertebra (% BMC change) |
|---|---|---|---|---|
| Exemplified fusion compound (0.5 mg/kg) | 9 | weekly | 0 | 6 |
| Exemplified fusion compound (2 mg/kg) | 10 | weekly | 24 | 26 |
| Exemplified fusion compound (0.5 mg/kg) | 9 | twice/week | 17 | 12 |
| Exemplified fusion compound (2 mg/kg) | 10 | twice/week | 46 | 38 |
| Rank mAb Alone (2 mg/kg) | 9 | twice/week | 19 | 13 |
| PTH peptide (5 µg/kg) | 9 | daily | 16 | 1 |
| Rank mAb (2 mg/kg) + PTH peptide (5 µg/kg) | 9 | twice/week + daily | 39 | 24 |

The results presented in Table 7 demonstrate that the exemplified fusion compound of the present invention demonstrates a dose-dependent increase of both BMD (of distal femur) and BMC (of lumbar vertebra) over RANKL antibody only and PTH peptide only treated mice, and compares favorably to co-administration of RANKL antibody and PTH peptide treated mice.

Pharmacodynamic Effects, In Vivo, in Cynomolgus Monkey Model

In vivo pharmacodynamic effects on serum calcium, bone formation biomarker P1NP, bone resorption biomarker CTx, and arterial pressure are assessed using cynomolgus monkey model as set forth in detail below. The data presented below demonstrates the exemplified fusion compound, unlike RANKL mAb-only treated animals, stimulates an increase (relative to baseline) in serum bone formation biomarker P1NP; stimulates a decrease (relative to baseline) of bone resorption biomarker CTx at a level similar to that seen in RANKL mAb-only treated animals; does not impact serum calcium concentrations relative to control-treated groups; and does not stimulate a mean difference in arterial pressure between treated and untreated groups of greater than 10 mm Hg for at least the first 8 hours post-treatment.

Serum Calcium Effects in Cynomolgus Monkey Model

Effect on serum calcium is assessed using a cynomolgus monkey model. Female cynomolgus monkeys aged five to six years receive a single subcutaneous injection of either 0.1 mg/kg of the exemplified fusion compound or a PBS vehicle control, or 1.0 mg/kg of the exemplified fusion compound or a PBS vehicle control. Additionally, male cynomolgus monkeys aged two to three years receive a single subcutaneous injection of either 0.1 mg/kg or 1.0 mg/kg of the exemplified fusion compound or PBS vehicle control.

Blood samples are collected from the femoral vein of each monkey prior to dosing and at twenty-four hour intervals thereafter for one week. Serum calcium concentrations of each collected sample are analyzed using a Roche P800 Modular Chemistry Analyzer (Roche Diagnostics Corp., Indianapolis Ind.). Results are presented in Table 8.

TABLE 8

Total Serum Calcium in Cynomolgus Monkeys (NC = sample not collected; ND = not determined).

| Molecule | N | Sex | Total Mean (±SD where applicable) Serum Calcium (mg/dL) Days pre/post-dosing | | | | | |
|---|---|---|---|---|---|---|---|---|
| | | | −1 | 0 | 0.5 | 1 | 2 | 3 |
| Exemplified fusion compound (0.1 mg/kg) | 3 | F | 10.6 ± 0.8 | NC | 10.0 ± 0.4 | 10.6 ± 0.6 | 10.0 ± 0.7 | 10.1 ± 0.3 |
| Vehicle control | 4 | F | 11.2 ± 0.6 | NC | 10.2 ± 0.5 | 10.7 ± 0.5 | 10.6 ± 0.8 | 10.4 ± 0.7 |
| Exemplified fusion compound (1.0 mg/kg) | 3 (except where noted) | F | 10.6 (N = 2) | NC | 9.8 ± 0.7 | 11.1 ± 0.6 | 10.6 ± 0.9 | 10.7 ± 0.3 |
| Vehicle control | 3 | F | 10.4 ± 0.3 | NC | 8.8 ± 0.2 | 10.0 ± 0.3 | 10.5 ± 1.0 | 10.4 ± 0.5 |
| Exemplified fusion compound (0.1 mg/kg) | 2 | M | 10.0 | 10.0 | NC | NC | 9.7 | 9.6 |
| Vehicle control | 3 | M | 10.3 ± 0.2 | 10.3 ± 0.2 | NC | NC | 10.0 ± 0.1 | 10.1 ± 0.5 |
| Exemplified fusion compound (1.0 mg/kg) | 3 | M | 10.3 ± 0.4 | NC | 11.7 ± 0.4 | 9.0 ± 0.5 | 9.1 ± 0.5 | 8.3 ± 0.8 |
| Vehicle control | 3 | M | 10. ± 0.4 | NC | 11.0 ± 1.1 | 9.4 ± 0.4 | 9.5 ± 0.2 | 9.2 ± 0.4 |

| Molecule | Total Mean (±SD where applicable) Serum Calcium (mg/dL) Days pre/post-dosing | | | | | | |
|---|---|---|---|---|---|---|---|
| | 4 | 5 | 6 | 7 | 8 | 9 | 10 |
| Exemplified fusion compound (0.1 mg/kg) | 10.3 ± 1.0 | 10.4 ± 0.4 | 10.4 ± 0.7 | 9.8 ± 0.4 | 10.1 ± 0.6 | NC | NC |
| Vehicle control | 10.3 ± 0.7 | 10.1 ± 0.4 | 10.4 ± 0.7 | 10.2 ± 0.9 | 10.2 ± 0.4 | NC | NC |
| Exemplified fusion compound (1.0 mg/kg) | 9.2 ± 0.8 | 10.2 ± 0.6 | 10.1 ± 0.6 | 9.7 ± 0.2 | 10.2 ± 0.6 | 10.0 ± 0.5 | 10.1 ± 1.1 |
| Vehicle control | 9.5 ± 1.1 | 9.8 ± 0.5 | 9.9 ± 0.8 | 9.7 ± 0.5 | 9.8 ± 0.3 | 9.6 ± 0.4 | 9.5 ± 0.1 |
| Exemplified fusion compound (0.1 mg/kg) | 9.0 | 9.8 | 9.8 | 10.1 | 10.0 | 10.4 | NC |
| Vehicle control | 10.5 ± 0.5 | 10.3 ± 0.3 | 10.9 ± 0.6 | 10.3 ± 0.3 | 10.6 ± 0.3 | 10.2 ± 0.2 | 10.2 ± 0.2 |
| Exemplified fusion compound (1.0 mg/kg) | 8.6 ± 0.7 | 9.5 ± 0.2 | NC | 6.8 ± 0.2 | 9.7 ± 0.8 | 8.7 ± 1.3 | 8.7 ± 0.7 |
| Vehicle control | 9.4 ± 0.3 | 10.5 ± 0.3 | NC | 10.1 ± 0.2 | 10.2 ± 0.5 | 10.1 ± 0.2 | 10.4 ± 0.6 |

The results presented in Table 8 demonstrate the exemplified fusion compound has no impact, relative to control dosed animals, on serum calcium levels in female cynomolgus monkeys at either dose concentration. The results presented in Table 8 also demonstrate the exemplified fusion compound has no impact, relative to control dosed animals, on serum calcium levels in male cynomolgus monkeys at 0.1 mg/kg. Monkeys dosed at a concentration of exemplified fusion compound at 1.0 mg/kg show a decrease, relative to control dosed animals, in serum calcium only at day 7 (on day 8, however, serum calcium levels had returned to levels equivalent that of control dosed animals).

Bone Formation Biomarker P1NP Effects in Cynomolgus Monkey Model

Effects on serum bone formation biomarker P1NP are assessed using a cynomolgus monkey model. Female cynomolgus monkeys aged five to six years receive a single subcutaneous injection of either: 0.1 mg/kg of the exemplified fusion compound or a PBS vehicle control; or 1.0 mg/kg of the exemplified fusion compound or a PBS vehicle control. Additionally, male cynomolgus monkeys aged two to three years receive a single subcutaneous injection of either 0.1 mg/kg or 1.0 mg/kg of the exemplified fusion compound; 0.1 mg/kg or 1.0 mg/kg of RANKL neutralizing antibody (an IgG4 RANKL mAb having the same HC and LC amino acid sequences as the mAb portion of the exemplified fusion compound); or a PBS vehicle control.

Blood samples are collected from the femoral vein of each monkey prior to dosing and at twenty-four hour intervals thereafter for one week. Serum P1NP concentrations of each collected sample are analyzed using a UNIQ™ P1NP RIA assay (Orion Diagnostica, Espoo, Finland). Results are presented in Table 9 as a mean % change from baseline P1NP concentrations (e.g., P1NP concentration at day 0).

TABLE 9

% Change in Serum P1NP Levels in Cynomolgus Monkeys.

| Molecule | N | Sex | Mean Percent Change (±SD where applicable) from Baseline in Serum P1NP Levels Days pre/post-dosing | | | | | |
|---|---|---|---|---|---|---|---|---|
| | | | 0 | 1 | 2 | 3 | 4 | 5 |
| Exemplified fusion compound (0.1 mg/kg) | 3 | F | NC | −2.92 ± 6.62 | −1.04 ± 4.86 | −29.91 ± 7.82 | −32.77 ± 3.45 | −15.05 ± 10.33 |
| Vehicle control | 3 | F | NC | 13.16 ± 25.17 | 20.73 ± 36.75 | 18.73 ± 22.19 | 18.00 ± 28.25 | 27.81 ± 20.53 |
| Exemplified fusion compound (1.0 mg/kg) | 3 | F | NC | −21.86 ± 3.33 | −55.09 ± 7.16 | −45.66 ± 12.22 | −25.26 ± 13.57 | −7.95 ± 9.22 |
| Vehicle control | 3 | F | NC | −14.03 ± 11.76 | −9.60 ± 11.91 | −12.16 ± 20.96 | −15.05 ± 13.30 | −11.84 ± 12.46 |
| Exemplified fusion compound (0.1 mg/kg) | 2 | M | 2.00 | −26.01 | −8.36 | −7.00 | 32.82 | 7.19 |
| Vehicle control | 3 | M | −5.69 + 6.61 | 2.7647 + 28.98 | −4.44 + 21.82 | −8.81 + 18.77 | −0.93 + 23.74 | 8.06 + 21.16 |
| Exemplified fusion compound (1.0 mg/kg) | 3 | M | −6.16 ± 8.45 | −45.09 ± 28.85 | −27.07 + 31.06 | 8.50 + 23.35 | 79.24 + 17.65 | 96.12 + 25.69 |
| Vehicle control | 3 | M | −1.54 ± 4.50 | −8.27 ± 3.81 | −7.32 ± 12.43 | −6.72 ± 9.41 | 22.61 ± 22.89 | 5.28 ± 30.43 |
| RANKL mAb (0.1 mg/kg) | 3 | M | 0 ± 0 | −26.56 ± 11.63 | −21.92 ± 12.70 | −29.43 ± 4.01 | −20.77 ± 5.82 | −34.27 ± 3.71 |
| RANKL mAb (1.0 mg/kg) | 3 | M | 0 ± 0 | −31.10 + 17.74 | −41.68 ± 7.58 | −42.40 ± 3.69 | −39.48 ± 10.09 | −48.68 ± 10.03 |

| Molecule | Mean Percent Change (±SD where applicable) from Baseline in Serum P1NP Levels Days pre/post-dosing | | | | | |
|---|---|---|---|---|---|---|
| | 6 | 7 | 8 | 9 | 10 | 16 |
| Exemplified fusion compound (0.1 mg/kg) | −6.43 ± 9.04 | −2.80 ± 13.31 | 3.53 ± 3.11 | 6.47 ± 12.44 | 19.16 ± 3.85 | 31.92 ± 24.52 |
| Vehicle control | 14.99 ± 14.98 | 27.54 ± 12.88 | 25.91 ± 13.66 | 22.34 ± 18.95 | 23.01 ± 16.02 | 25.22 ± 28.95 |
| Exemplified fusion compound (1.0 mg/kg) | 15.71 ± 2.72 | 15.63 ± 7.20 | 19.62 ± 7.79 | 30.25 ± 21.86 | 24.62 ± 8.84 | 28.69 ± 12.36 |
| Vehicle control | −7.16 ± 13.90 | −17.08 ± 12.09 | −17.53 ± 10.76 | −22.57 ± 16.91 | −12.06 ± 11.73 | −13.85 ± 21.88 |
| Exemplified fusion compound (0.1 mg/kg) | −10.55 | −16.58 | 15.93 | 13.77 | NC | −16.98 |
| Vehicle control | −1.65 + 19.84 | −6.02 + 18.42 | 0.21 + 26.52 | −3.94 + 25.91 | NC | −7.64 + 19.22 |
| Exemplified fusion compound (1.0 mg/kg) | NC | 21.34 ± 9.52 | NC | 43.80 + 18.82 | NC | 47.04 + 11.04 |
| Vehicle control | NC | −19.59 ± 16.35 | NC | −13.47 ± 16.26 | NC | 3.51 ± 9.86 |
| RANKL mAb (0.1 mg/kg) | NC | −32.45 ± 7.74 | NC | NC | −32.08 ± 12.29 | NC |

TABLE 9-continued

| % Change in Serum P1NP Levels in Cynomolgus Monkeys. | | | | | | |
|---|---|---|---|---|---|---|
| RANKL mAb (1.0 mg/kg) | NC | −50.50 + 6.72 | NC | NC | −57.22 ± 5.32 | NC |

The results presented in Table 9 demonstrate that, after a single dose of either 0.1 or 1.0 mg/kg, the exemplified fusion compound (unlike RANKL mAb-only treated animals), stimulates a dose-dependent increase in serum P1NP levels in both male and female monkeys relative to control treated animals. RANKL mAb-only treated animals demonstrate a decrease in serum P1NP levels in both male and female monkeys relative to control treated animals.

Bone Resorption Biomarker CTx Effects in Cynomolgus Monkey Model

Effects on serum bone resorption biomarker CTx are assessed using a cynomolgus monkey model. Male cynomolgus monkeys aged two to three years receive a single subcutaneous injection of either: 0.1 mg/kg or 1 mg/kg of the exemplified fusion compound; 0.1 mg/kg or 1.0 mg/kg of RANKL neutralizing antibody (an IgG4 RANKL mAb having the same HC and LC amino acid sequences as the mAb portion of the exemplified fusion compound); or a PBS vehicle control. Additionally, female cynomolgus monkeys aged five to six years receive a single subcutaneous injection of either 0.1 mg/kg or 1.0 mg/kg of the exemplified fusion compound.

Blood samples are collected from the femoral vein of each monkey prior to dosing and at twenty-four hour intervals thereafter for one week. Serum CTx concentrations of each collected sample are analyzed using ELISA method per manufacture's instruction. (Immunodiagnostic Systems Inc.). Results are presented in Table 10 as mean % change from baseline in serum CTx concentrations (e.g., CTx concentration at day 0).

TABLE 10

| Serum CTx Levels in Cynomolgus Monkeys. | | | | | | | |
|---|---|---|---|---|---|---|---|
| | | | Mean Percent Change (±SD where applicable) from Baseline in Serum CTx Days post-dosing | | | | |
| Molecule | N | Sex | 0 | 1 | 2 | 3 | 4 |
| Exemplified fusion compound (0.1 mg/kg) | 3 | F | NC | 26.03 ± 55.00 | −49.06 ± 32.81 | −44.08 ± 22.07 | −52.34 ± 10.94 |
| Vehicle control | 3 | F | NC | −13.66 ± 40.37 | 0.76 ± 25.07 | −23.52 ± 21.09 | −16.12 ± 35.68 |
| Exemplified fusion compound (1.0 mg/kg) | 3 (except where noted) | F | NC | −20.50 ± 27.29 | −52.02 ± 17.11 | −68.82 ± 5.17 | −66.73 ± 9.61 |
| Vehicle control | 3 | F | NC | 26.70 ± 12.66 | 47.79 ± 7.32 | 43.29 ± 25.16 | 46.39 ± 42.97 |
| Exemplified fusion compound (0.1 mg/kg) | 2 | M | 3.29 | −23.14 | −56.08 | −50.52 | −45.72 |
| Vehicle control | 3 | M | −5.68 ± 10.28 | −33.02 ± 11.30 | −2.75 ± 21.19 | 2.48 ± 32.61 | −2.51 ± 27.10 |
| Exemplified fusion compound (1.0 mg/kg) | 3 | M | −1.45 ± 13.62 | −32.50 + 11.15 | −63.03 + 6.09 | −65.67 + 11.75 | −67.21 + 14.11 |
| Vehicle control | 3 | M | 17.05 ± 9.97 | −12.04 ± 30.16 | −39.88 ± 4.83 | −15.25 ± 15.01 | −15.25 ± 9.95 |
| RANKEL mAb (0.1 mg/kg) | 6 | M | 0 ± 0 | −49.32 ± 6.93 | −29.83 ± 22.69 | −41.11 ± 11.58 | −60.32 ± 8.75 |
| RANKEL mAb (1.0 mg/kg) | 3 | M | 0 ± 0 | −61.37 + 1.32 | −58.89 ± 8.28 | −64.36 ± 8.41 | −77.70 ± 0.38 |

| | Mean Percent Change (±SD where applicable) from Baseline in Serum CTx Days post-dosing | | | | | |
|---|---|---|---|---|---|---|
| Molecule | 5 | 6 | 7 | 8 | 9 | 10 |
| Exemplified fusion compound (0.1 mg/kg) | −43.25 ± 6.95 | −31.24 ± 10.12 | −22.77 ± 6.47 | −22.89 ± 10.39 | −20.65 ± 11.22 | −29.29 ± 24.20 |

TABLE 10-continued

Serum CTx Levels in Cynomolgus Monkeys.

| | | | | | | |
|---|---|---|---|---|---|---|
| Vehicle control | −13.64 ± 39.17 | −15.22 ± 26.67 | −15.43 ± 22.75 | −26.97 ± 8.18 | −21.27 ± 26.03 | 7.2213 ± 35.54 |
| Exemplified fusion compound (1.0 mg/kg) | −67.65 ± 13.75 | −70.07 ± 7.15 | −69.20 ± 15.01 | −67.24 ± 9.46 | −68.19 ± 17.41 | −62.46 ± 11.29 |
| Vehicle control | 55.54 ± 57.18 | 63.37 ± 71.66 | 68.26 ± 86.77 | 73.74 ± 102.74 | 79.19 ± 119.35 | 92.41 ± 128.03 |
| Exemplified fusion compound (0.1 mg/kg) | −47.30 | −13.26 | −25.46 | −18.61 | −27.29 | NC |
| Vehicle control | −10.43 ± 22.82 | −4.15 ± 34.72 | −1.80 ± 29.84 | 3.537707 | 15.19 ± 11.56 | NC |
| Exemplified fusion compound (1.0 mg/kg) | −66.17 + 13.95 | NC | −69.30 + 8.27 | NC | −64.36 + 14.50 | NC |
| Vehicle control | −2.22 ± 19.06 | NC | 26.93 ± 10.66 | NC | −28.87 ± 5.85 | NC |
| RANKEL mAb (0.1 mg/kg) | −64.90 ± 3.43 | NC | −28.04 ± 12.42 | NC | NC | −16.63 ± 8.43 |
| RANKEL mAb (1.0 mg/kg) | −76.0411 ± 2.44 | NC | −75.22 + 4.81 | NC | NC | −71.80 + 7.89 |

The results presented in Table 10 demonstrate that after a single dose of either 0.1 or 1.0 mg/kg of the exemplified fusion compound, in both male and female monkeys, serum CTx levels are reduced relative to control-treated monkeys (and reduced to levels similar to the RANKL mAb-only treated groups).

Arterial Pressure Effects in Cynomolgus Monkey Model

Effects on arterial pressure are assessed using a female cynomolgus monkey model. Female cynomolgus monkeys, aged five to six years, receive a single subcutaneous injection of either: 0.1 mg/kg or 1.0 mg/kg of the exemplified fusion compound; or of PBS vehicle control. Mean arterial pressure is measured for each animal at one-hour intervals for the first eight hours post-injection. A baseline arterial pressure for each animal is measured at time point 0. Results are presented in Table 11, including the mean difference in mmHg between treated and control groups (adjusted for baseline correction).

TABLE 11

Mean Arterial Pressure in Cynomolgus Monkeys.

| | | Mean Arterial Pressure (mm Hg) ± SD from Baseline hours post-dosing | | | | | | | | |
|---|---|---|---|---|---|---|---|---|---|---|
| Molecule | N | 0 | 1 | 2 | 3 | 4 | 5 | 6 | 7 | 8 |
| Exemp. fusion cmpd 0.1 mg/kg | 3 | 77.71 (0.93) | 85.15 (3.00) | 64.79 (6.90) | 65.08 (5.59) | 64.50 (2.50) | 62.42 (7.21) | 66.23 (10.75) | 64.17 (3.96) | 68.61 (1.74) |
| Vehicle Control | 4 | 84.72 (6.06) | 85.81 (9.28) | 79.98 (7.83) | 78.84 (3.74) | 75.40 (2.43) | 72.81 (4.39) | 74.10 (3.84) | 76.90 (2.80) | 80.18 (5.68) |
| Mean difference | | +6.35 | −8.18 | −6.75 | −3.89 | −3.38 | −0.86 | −5.63 | −4.56 | +6.35 |
| Exemp. fusion cmpd 1.0 mg/kg | 3 | 84.72 (6.06) | 82.13 (11.92) | 77.34 (6.68) | 77.38 (6.18) | 74.73 (7.79) | 75.91 (10.27) | 74.14 (10.13) | 73.18 (8.27) | 73.59 (12.58) |
| Vehicle Control | 6 | 77.71 (0.93) | 75.24 (6.02) | 59.04 (9.18) | 61.54 (3.64) | 62.98 (5.90) | 67.52 (9.42) | 66.71 (7.24) | 67.86 (3.74) | 66.44 (2.95) |
| Mean difference | | +0.12 | +11.29 | +8.83 | +4.74 | +1.38 | +0.42 | −1.69 | +0.14 | +0.12 |

The results presented in Table 11 demonstrate that a single dose of 0.1 or 1.0 mg/kg of the exemplified fusion compound does not stimulate a mean difference in arterial pressure between treated and untreated groups of greater than 10 mm Hg for the first 8 hours post treatment (subsequent testing, data not shown, demonstrates the mean arterial pressure between treated and untreated groups does not exceed 10 mm Hg for at least 69 hours post-dosing).

Fusion Compound Physical and Chemical Property Analysis

Fusion Compound Solubility Analysis

Solubility of the exemplified fusion compound is analyzed at 4° C. after a 4 week incubation period. Solubility is assessed with fusion compound concentrated to between 100 and 150 mg/mL using a Millipore centrifugal filter device (p/n. #UFC803024). Samples are formulated in three buffers: (a) 10 mM citrate at pH 6.0; (b) 10 nM citrate at pH6.0 plus 150 mM NaCl; and (c) PBS at pH 7.4. The exemplified fusion compound exhibited a solubility of greater than 110 mg/mL for all formulations. Formulation (b), 10 nM citrate at pH6.0 plus 150 mM NaCl, exhibited a solubility of greater than 150 mg/mL.

Additionally, formulated samples (a-c, as described above) are analyzed for percent high molecular weight (% HMW) soluble aggregate using size exclusion chromatography (SEC) with a TSKGEL Super SW3000™ (Tosoh Bioscience product #18675) column. Samples are assayed both at 100 mg/mL and 1 mg/mL. Chromatograms are analyzed using Chem Station and % high molecular weight (HMW) is calculated using the ratio of AUC of the peaks eluted before the monomer peak to total AUC. Both formulations (a) and (b), at both 100 and 1mg/mL concentrations, exhibited less than a 5% increase in HMW soluble aggregate formation.

Low Concentration Freeze/Thaw Analysis

Low concentration freeze/thaw analysis of the exemplified fusion compound is assessed with fusion compound concentrated at 1 mg/ml and formulated in 10 mM citrate, pH 6.0, with and without 150 mM NaCl and with and without 0.02% TWEEN-80™ detergent (pH 5.5 and pH6.0, respectively). Three freeze/thaw cycles (a single cycle including incubation at −70° C. for at least four hours, followed by thawing at ambient temperature, then gentle mixing) are performed and particle growth for each sample is assessed using a HIAC Particle Counter (Pacific Scientific, p/n. 9703). Percent high molecular weight (% HMW) soluble aggregate using SEC is also assessed. Particle counts for both formulations (with and without 0.02% TWEEN-80™ detergent) are less than 400. Formulations with 0.02% TWEEN-80™ detergent demonstrated a reduction in particle counts. Additionally, all formulations exhibit less than a 5% increase in HMW soluble aggregate formation. These results demonstrate the exemplified fusion compound of the present invention, under low concentration conditions, is stable following multiple freeze/thaw cycles.

High Concentration Physical Stability Analysis

High concentration freeze/thaw analysis of the exemplified bispecific antibody is assessed with bispecific antibody concentrated at 50 mg/ml and formulated in either 10 mM citrate, pH 6.0 with 150 mM NaCl or 10 mM citrate, pH 6.0, 0.02% TWEEN-80™ detergent, with 150 mM NaCl. Samples are either incubated for four weeks at 4° C., 25° C., or subjected to three freeze/thaw cycles (a single cycle including incubation at −70° C. for at least four hours, followed by thawing at ambient temperature, then gentle mixing). Following the respective incubation or freeze thaw period, samples are analyzed for particle growth using HIAC Particle Counter or % HMW soluble aggregate using SEC. Particle counts for both formulations under all treatment conditions are less than 1000. Additionally, all formulations exhibited less than a 6.5% increase in HMW soluble aggregate formation. These results demonstrate the exemplified fusion compound of the present invention, under high concentration conditions, is stable following incubation under various conditions and multiple freeze/thaw cycles.

Sequences
SEQ ID NO: 1 - Exemplified First Polypeptide (of exemplified fusion compound of Table 1)
SVSEIQLMHNLGKHLNSMERVEWLRKKLQDVHNFGGGGSGGGGSGGGGSQ

VQLVQSGAEVKKPGSSNIKVSCKASGYAFTNYYIEWVRQAPGQGLEWMGV

INPGWGDTNYNEKFKGRVTITADKSTSTAYMELSSLASEDTAVYYCARRD

TAHGYYALDPWGQGTTVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLG

SEQ ID NO: 2 - Exemplified Second Polypeptide (of the exemplified fusion compound of Table 1)
DIQMTQSPSSLSASVGDRVTITCKASQNVGTNVAWYQQKPGKAPKLLIYS

ASYRYSGVPSRFSGSGSGTDFTLTISSLQPEDFATYYCQQYWDYPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 3 - DNA Seq. Encoding the Exemplified First Polypeptide (SEQ ID NO. 1) and a Signal Peptide
AGCGTGTCCGAGATCCAGCTGATGCACAACCTCGGCAAGCACCTGAATAG

CATGGAGCGCGTCGAGTGGCTGCGGAAGAAACTGCAGGACGTGCACAACT

TCGGCGGCGGCGGCAGCGGCGGTGGCGGCTCCGGTGGCGGCGGAAGCCAG

GTGCAGCTGGTGCAGTCTGGGGCTGAGGTGAAGAAGCCTGGGTCCTCAGT

GAAGGTTTCCTGCAAGGCATCTGGCTACGCCTTCACCAACTACTATATCG

AGTGGGTGCGACAGGCCCCTGGACAAGGGCTTGAGTGGATGGGAGTGATC

AACCCCGGCTGGGGCGACACGAACTACAACGAGAAGTTCAAGGGCAGAGT

CACCATTACCGCGGACAAATCCACGAGCACAGCCTACATGGAGCTGAGCA

GCCTGAGATCTGAGGACACGGCCGTGTATTACTGTGCGAGACGCGATACG

GCTCACGGCTACTACGCCCTTGATCCGTGGGGCCAAGGAACCACGGTCAC

CGTCTCCTCAGCCTCCACCAAGGGCCCATCGGTCTTCCCGCTAGCGCCCT

GCTCCAGGAGCACCTCCGAGAGCACAGCCGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCTGTCCTACAGTCCTCAGGACTCTACT

CCCTCAGCAGCGTGGTGACCGTGCCCTCCAGCAGCTTGGGCACGAAGACC

TACACCTGCAACGTAGATCACAAGCCCAGCAACACCAAGGTGGACAAGAG

AGTTGAGTCCAAATATGGTCCCCCATGCCCACCCTGCCCAGCACCTGAGG

CCGCCGGGGGACCATCAGTCTTCCTGTTCCCCCCAAAACCCAAGGACACT

CTCATGATCTCCCGGACCCCTGAGGTCACGTGCGTGGTGGTGGACGTGAG

CCAGGAAGACCCCGAGGTCCAGTTCAACTGGTACGTGGATGGCGTGGAGG

TGCATAATGCCAAGACAAAGCCGCGGGAGGAGCAGTTCAACAGCACGTAC

CGTGTGGTCAGCGTCCTCACCGTCCTGCACCAGGACTGGCTGAACGGCAA

GGAGTACAAGTGCAAGGTCTCCAACAAAGGCCTCCCGTCCTCCATCGAGA

AAACCATCTCCAAAGCCAAAGGGCAGCCCCGAGAGCCACAGGTGTACACC

CTGCCCCCATCCCAGGAGGAGATGACCAAGAACCAGGTCAGCCTGACCTG

CCTGGTCAAAGGCTTCTACCCCAGCGACATCGCCGTGGAGTGGGAAAGCA

ATGGGCAGCCGGAGAACAACTACAAGACCACGCCTCCCGTGCTGGACTCC

GACGGCTCCTTCTTCCTCTACAGCAGGCTAACCGTGGACAAGAGCAGGTG

GCAGGAGGGGAATGTCTTCTCATGCTCCGTGATGCATGAGGCTCTGCACA

ACCACTACACACAGAAGAGCCTCTCCCTGTCTCTGGGTTGA

SEQ ID NO: 4 - DNA Seq. Encoding the Exemplified
Second Polypeptide (SEQ ID NO. 2) and a Signal
Peptide
GGCGGCGGCGGCAGCGGCGGTGGCGGCTCCGGTGGCGGCGGAAGCGACAT

CCAGATGACCCAGTCTCCATCCTCTCTGTCTGCATCTGTAGGAGACAGAG

TCACCATCACTTGCAAGGCCAGCCAGAATGTGGGCACCAACGTGGCCTGG

TATCAGCAGAAACCAGGGAAAGCCCCTAAGCTCCTGATCTATAGCGCCAG

CTACAGATACAGCGGGGTCCCATCAAGGTTCAGTGGCAGTGGATCTGGGA

CAGATTTCACTCTCACCATCAGCAGTCTGCAACCTGAAGATTTTGCAACT

TACTACTGTCAGCAGTACTGGGACTACCCCCTGACCTTCGGCGGAGGGAC

CAAGGTGGAGATCAAACGGACTGTGGCTGCACCATCTGTCTTCATCTTCC

CGCCATCTGATGAGCAGTTGAAATCTGGAACTGCCTCTGTTGTGTGCCTG

CTGAATAACTTCTATCCCAGAGAGGCCAAAGTACAGTGGAAGGTGGATAA

CGCCCTCCAATCGGGTAACTCCCAGGAGAGTGTCACAGAGCAGGACAGCA

AGGACAGCACCTACAGCCTCAGCAGCACCCTGACGCTGAGCAAAGCAGAC

TACGAGAAACACAAAGTCTACGCCTGCGAAGTCACCCATCAGGGCCTGAG

CTCGCCCGTCACAAAGAGCTTCAACAGGGGAGAGTGCTAA

SEQ ID NO: 5 - Exemplified HCVR (of exemplified
fusion compound of Table 1)
QVQLVQSGAEVKKPGSSVKVSCKASGYAFTNYYIEWVRQAPGQGLEWMGV

INPGWGDTNYNEKFKGRVTITADKSTSTAYMELSSLASEDTAVYYCARRD

TAHGYYALDPWGQGTTVTVSS

SEQ ID NO: 6 - Exemplified LCVR (of exemplified
fusion compound of Table 1)
DIQMTQSPSSLSASVGDRVTITCKASQNVGTNVAWYQQKPGKAPKLLIYS

ASYRYSGVPSRFSGSGSGTDFTLTISSLQPEDFATYYCQQYWDYPLTFGG

GTKVEIK

SEQ ID NO: 7 - Exemplified HCDR1 (of exemplified
fusion compound of Table 1)
GYAFTNYYIE SEQ ID NO: 8 - Exemplified HCDR2 (of exemplified
fusion compound of Table 1)
VINPGWGDTNYNEKFKG SEQ ID NO: 9 - Exemplified HCDR3 (of exemplified
fusion compound of Table 1)
RDTAHGYYALDP SEQ ID NO: 10 - Exemplified LCDR1 (of exemplified
fusion compound of Table 1)
KASQNVGTNVA SEQ ID NO: 11 - Exemplified LCDR2 (of exemplified
fusion compound of Table 1)
SASYRYS SEQ ID NO: 12 - Exemplified LCDR3 (of exemplified
fusion compound of Table 1)
QQYWDYPLT SEQ ID NO: 13 - Exemplified PTH Peptide of
exemplified fusion compound of Table 1
SVSEIQLMHNLGKHLNSMERVEWLRKKLQDVHNF SEQ ID NO: 14 - Exemplified Linker of exemplified
fusion compound of Table 1
GGGGSGGGGSGGGGS SEQ ID NO: 15 - Full length Human Parathyroid
Hormone
SVSEIQLMHN LGKHLNSMER VEWLRKKLQD VHNFVALGAP

LAPRDAGSQR PRKKEDNVLV ESHEKSLGEA DKADVNVLTK AKSQ

---

We claim:

1. A compound comprising a first polypeptide and a second polypeptide, wherein
   a) said first polypeptide comprises a parathyroid hormone (PTH) peptide and a monoclonal antibody (mAb) IgG heavy chain (HC), the PTH peptide having the amino acid sequence given by SEQ ID NO: 13, and the HC having a heavy chain variable region (HCVR) comprising heavy chain complementary determining regions (HCDR) 1-3, HCDR1 having the amino acid sequence given by SEQ ID NO: 7, HCDR2 having the amino acid sequence given by SEQ ID NO: 8, and HCDR3 having the amino acid sequence given by SEQ ID NO: 9; and
   b) said second polypeptide comprises a mAb light chain (LC) comprising a light chain variable region (LCVR) comprising light chain complementary determining regions (LCDR) 1-3, LCDR1 having the amino acid sequence given by SEQ ID NO: 10, LCDR2 having the amino acid sequence given by SEQ ID NO: 11, and LCDR3 having the amino acid sequence given by SEQ ID NO: 12,
   wherein the PTH peptide is linked to the HC via a polypeptide linker (L1), L1 being covalently attached to the N-terminus of HC and the C-terminus of the PTH peptide.

2. The compound of claim 1, wherein the HCVR has the amino acid sequence given by SEQ ID NO: 5 and the LCVR has the amino acid sequence given by SEQ ID NO: 6.

3. The compound of claim 1, wherein L1 has the amino acid sequence given by SEQ ID NO: 14.

4. The compound of claim 3, wherein the first polypeptide has the amino acid sequence given by SEQ ID NO: 1 and the second polypeptide has the amino acid sequence given by SEQ ID NO: 2.

5. The compound of claim 4 comprising two first polypeptides and two second polypeptides.

6. A pharmaceutical composition comprising a compound of claim 1 and one or more pharmaceutically acceptable carriers, diluents, or excipients.

7. The compound of claim 2, wherein L1 has the amino acid sequence given by SEQ ID NO: 14.

8. A DNA molecule comprising a polynucleotide sequence encoding the first polypeptide and the second polypeptide of the compound of claim 1, the first polypeptide having the amino acid sequence of SEQ ID NO: 1 and the second polypeptide having the amino acid sequence of SEQ ID NO: 2.

9. An isolated mammalian cell comprising the DNA molecule of SEQ ID NO: 3 and the DNA molecule of SEQ ID NO:4, which cell is capable of expressing polypeptides comprising the first polypeptide and the second polypeptide of the compound of claim 1, the first polypeptide having the amino acid sequence of SEQ ID NO: 1 and the second polypeptide having the amino acid sequence of SEQ ID NO: 2.

10. The mammalian cell of claim 9, wherein the mammalian cell is a Chinese Hamster Ovary cell.

11. An isolated mammalian cell comprising the DNA molecule of claim 8, which cell is capable of expressing the first polypeptide and the second polypeptide.

12. The mammalian cell of claim 11, wherein the mammalian cell is a Chinese Hamster Ovary cell.

13. A process for producing a compound comprising a first polypeptide having the amino acid sequence given by SEQ ID NO: 1 and a second polypeptide having the amino acid sequence given by SEQ ID NO: 2, comprising cultivating the mammalian cell of claim 11 under conditions such that the compound is expressed, and recovering the expressed compound.

14. A process for producing a compound comprising a first polypeptide having the amino acid sequence given by SEQ ID NO: 1 and a second polypeptide having the amino acid sequence given by SEQ ID NO: 2, the process comprising cultivating the mammalian cell of claim 9 under conditions such that the compound is expressed, and recovering the expressed compound.

15. A compound produced by the process of claim 13.

16. A compound produced by the process of claim 14.

17. A method of treating a bone disorder, comprising administering to a patient in need thereof a therapeutically effective amount of a compound of claim 1.

18. The method of claim 17, wherein the bone disorder is osteoporosis.

19. The method of claim 17, wherein the bone disorder is selected from the group consisting of: osteopenia, osteogenesis imperfecta, transplant-associated bone loss, autoimmune-induced bone loss, disuse-induced bone loss, degenerative lumbar spondylolisthesis, and degenerative disk disease.

* * * * *